United States Patent [19]

Mascellani et al.

[11] Patent Number: 4,973,580

[45] Date of Patent: Nov. 27, 1990

[54] DEPOLYMERIZED DERMATAN SULFATES ENDOWED WITH AN ANTITHROMBOTIC, FIBRINOLYTIC, ANTIINFLAMMATORY ACTIVITY AND PHARMACEUTICAL COMPOSITIONS CONTAINING SUCH

[75] Inventors: Giuseppe Mascellani; Pietro Bianchini, both of Corlo, Italy

[73] Assignee: Opocrin S.P.A. Laboratorio Farmacobiologico, Corlo, Italy

[21] Appl. No.: 349,706

[22] Filed: May 10, 1989

Related U.S. Application Data

[63] Continuation of Ser. No. 6,497, filed as PCT EP86/00291 on May 15, 1986, published as WO86/06729 on Nov. 20, 1986, abandoned.

[30] Foreign Application Priority Data

May 17, 1985 [IT] Italy ................... 20769 A/85

[51] Int. Cl.$^5$ ............... A61K 31/725; C08B 37/00; C08B 37/10
[52] U.S. Cl. ......................... 514/54; 536/21; 536/54; 536/55.1; 514/56
[58] Field of Search ............ 536/21, 55.2, 55.3, 536/122, 123, 124, 18.5, 4.1, 54, 55.1; 514/53, 54, 56, 822

[56] References Cited

U.S. PATENT DOCUMENTS

| | | | |
|---|---|---|---|
| B 408,030 | 1/1975 | Speakman | 536/102 |
| 3,247,063 | 4/1966 | Pulver | 514/54 |
| 4,281,108 | 7/1981 | Fussi | 536/21 |
| 4,496,550 | 1/1985 | Lindahl et al. | 514/54 |
| 4,524,066 | 6/1985 | Wolf | 514/54 |
| 4,533,549 | 8/1985 | Lasker | 514/56 |
| 4,687,765 | 8/1987 | Vairel et al. | 514/56 |
| 4,745,108 | 5/1988 | Foley et al. | 514/56 |
| 4,757,057 | 7/1988 | Fussi et al. | 514/56 |
| 4,791,195 | 12/1988 | Bianchini et al. | 536/21 |
| 4,804,652 | 2/1989 | Lormeau et al. | 514/56 |

FOREIGN PATENT DOCUMENTS

| | | |
|---|---|---|
| 0101141 | 2/1984 | European Pat. Off. . |
| 0121067 | 10/1984 | European Pat. Off. . |
| 62-4703 | 1/1987 | Japan . |

OTHER PUBLICATIONS

Tollefsen; Nouv. Rev. Fr. Hematol., 26:233-237, (1984).

*Primary Examiner*—Ronald W. Griffin
*Assistant Examiner*—Nancy S. Carson
*Attorney, Agent, or Firm*—Bucknam and Archer

[57] ABSTRACT

Process for the preparation of oligosaccharides by a controlled chemical depolymerization of natural polysaccharides, such as heparins, heparan sulfates, dermatan sulfates, chondroitinsulfates, hyaluronic acid, by a radicalic reaction in an aqueous solution, at a temperature ranging between 20° and 70° C., in the presence of a catalyst selected in the group consisting of $Cu++$, $Fe++$, $Cr+++$, $Cr_2O_7-$ as well as the resulting oligosaccharides and their related pharmaceutical compositions. The products exhibit high antithrombotic activity, little or no anticoagulant activity, high fibrinolytic activity an antiinflammatory activity.

3 Claims, No Drawings

DEPOLYMERIZED DERMATAN SULFATES ENDOWED WITH AN ANTITHROMBOTIC, FIBRINOLYTIC, ANTIINFLAMMATORY ACTIVITY AND PHARMACEUTICAL COMPOSITIONS CONTAINING SUCH

This is a continuation of application Ser. No. 006,497, filed as PCT EP86/00291 on May 15, 1986, published as WO86/06729 on Nov. 20, 1986, now abandoned.

The present invention concerns a process for the preparation of oligosaccharides by a controlled chemical depolymerization of natural polysaccharides such as heparins, heparan sulfates, dermatan sulfates, chondroitinsulfates, hyaluronic acid.

The invention also concerns the new resulting products as well as their related pharmaceutical compositions.

Actually, the resulting products have a high capacity of inhibiting the Xa factor, a high antithrombotic activity, poor or no anticoagulant activity, a high fibrinolytic activity, and an antiinflammatory activity.

Said products are also endowed with a good bioavailability, after oral administration, deriving from the reduced molecular weight of the oligomers as compared with the starting polysaccharides.

The process of the invention consists in the depolymerization of a polysaccharide, in a 10–20% aqueous solution, at a temperature ranging between 30° and 70° C., by a radical reaction initiated by a peroxide or by a peracid such as peracetic acid, hydrogen peroxide, 3-chloro-perbenzoic acid, sodium persulfate, cumyl hydroperoxide, in the presence of catalytic amounts of a metal such as $Cu^{++}$ or $Fe^{++}$, or $Cr^{+++}$ or $Cr_2O_7^{---}$, etc., in a concentration ranging between 0.001 and 0.1M.

The depolymerization product is usually isolated at the solid state from the reaction solution, by precipitation with solvents or with quaternary ammonium bases.

The resulting oligosaccharides are usually salified with alkaline metals, such as sodium, potassium or lithium or with alkaline-earth metals such as calcium or magnesium.

Heparin with a low molecular weight, i.e. ranging between 3,500 and 8,000 daltons, has a marked antithrombotic activity associated with no or scarce anticoagulanr effect.

Moreover, fragments of dermatan sulfate, containing a minimum of 12–14 sugar residues, resulting from a degradation with periodic acid (Tollefsen DM. Nouv. Rev. Fr. Haematol., 26, 233, 1984) and fractionation on an affinity column, were reported to be endowed with a marked activity on the heparin cofactor II, this activity being higher than that of the unfractionated dermatan sulfate. On the other hand, no products of depolymerization of other chondroitin sulfates and heparan sulfates are known.

Various processes for the depolymerization of natural heparin were described in literature. A process, suited to obtain low molecular weight compounds, consists in the deaminarive hydrolysis of heparin with nitrous acid in a diluted solution The resulting compounds are characterized by a terminal residue consisting of 2,5-anhydromannose (I):

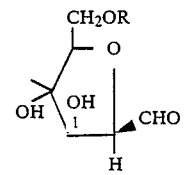

(U.S. Pat. No. 4,438,261; WO No. 82/03627, published on 10.28.1982; Eur. Pat. Appl. No. 0048231).

A process was described of alkaline hydrolysis on heparin (Eur. Pat. Appl. No. 0040144), or on heparin alkyl or aryl esters (Eur. Pat. Appl. No. 0044228), that, by β-elimination, leads to oligomers, with a mean molecular weight of 2,000–9,000 daltons. showing the unsaturated sugar (II) as the terminal group:

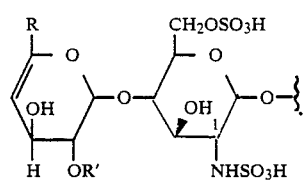

R' = H, $SO_3H$
R = COOH

The yields of said process are very low.

Another depolymerization process consists in the enzymatic hydrolysis of heparin by heparinase, in very diluted solutions and in a very low yield, with formation of sugar (III) and glucosamine in a hemiacetalic form (IV)

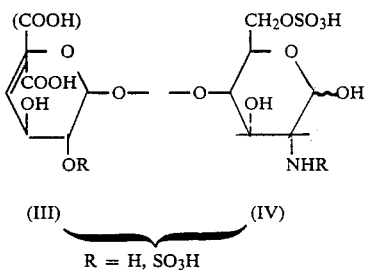

R = H, $SO_3H$ as terminal groups (Eur. Pat. Appl. No. 0064452; J. Biol. Chem., 257, 7310, 1982).

Processes of heparin depolymerization also described, based on the use of oxidizing agents, such as alkaline periodates, that oxidize the bond between the proximal $C_2$–$C_3$ hydroxyl groups of the unsulfated uronic acids, with consequent labilization of the glucosidic bond (Casu B. "Structure and Biological Activity of Heparin". Advances in Carbohydr. Chem. Biochem. Vol. 43, 1985, 51-134, Acad. Press).

Other processes are based on the combined action of hydrogen peroxide and of the acid pH on heparin, at a high temperature (125° C.) under pressure. A depolymerization occurs, with consequent alteration and potential impairment of the oligomers activity (Eur. Pat. Appl. No. 0101141, published on 8.22.1984).

Other processes are based on the acid depolymerization by sulfuric acid and a concurrent or subsequent resulfatation with a mixture of chlorosulfonic acid (Nagasawa K. et al., Arhiv. Biochem. Biophys., 150, 451, 1972; French Patent Appl. No. 2,538,404).

All these processes, described on a laboratory scale, are characterized by low yields and a poor reproducibility, essentially in the scaling up to a preindustrial and industrial scale.

The Italian Patent Application No. 40021 A/83, corresponding to the European Patent Application No. 0121067, describes a process that uses concurrently hydrogen peroxide, ascorbic acid and copper acetate for the attainment of oligosaccharides of a suited molecular weight.

Said invention considers quite prolonged times of reaction, i.e. up to 24–48 hours, and highly diluted solutions of heparin, with consequent low yields. Moreover, the depolymerization products result to be contaminated with ascorbic acid degradation products.

It has now been surprisingly found that any polysaccharide of the type of heparins, heparan sulfates, dermatan sulfates, chondroitin sulfates, hyaluronic acid can be depolymerized, in an aqueous solution at concentrations even higher than 10–15%, at temperatures ranging between 20° and 70° C., in a few hours time, by a radicalic reaction initiated by a radical e.g. the OH radical, generated in an aqueous solution from a peracid or a peroxide such as peracetic acid, hydrogen peroxide, 3-chloroperbenzoic acid, cumene hydroperoxide, sodium persulfate, benzoyl peroxide, in the presence of a catalyst, in a concentration ranging between 0.1M and 0.001M, consisting of a metal such as $Cu^{++}$, $Fe^{++}$, $Cr^{+++}$, or of an anhydride such as $Cr_2O_7^{--}$.

The process object of the present invention, offers the hereinbelow mentioned advantages over the already known methods:

rapidity of execution;

attainment of polysaccharides with the desired mean molecular weight;

possibility of operating also on a large scale, in high concentrations of biopolymer to be depolymerized, such as to require no subsequent and expensive processes of concentration and purification for the recovery of the depolymerized products.

The resulting oligosaccharides are substantially pure since the peroxide transformation products can be easily removed, and the catalyst metals can be sequestered by EDTA or by sequestering resins such as, for example, the ones carrying an iminodiacetic functional group.

No other contaminant is present in the reaction mass, unlike, for example, the case of the process of depolymerization based on the use of ascorbic acid that originates in turn dehydroascorbic, diketoglutaric, threonic and oxalic acids (Niedermeier W. et al., B.B.A., 141, 336, 1967), that are all possible contaminants of the depolymerized polysaccharides.

Actually, the low molecular weight products, obtained in the present process of depolymerization, can be directly isolated from the reaction medium, essentially in the form of sodium salts, at a pH level around neutrality, with a non-solvent agent such as methanol, ethanol, acetone, dioxane. The product can be purified by double precipitation or by dissolution, elution on a column of a suited resin, and reprecipitation with methanol or ethanol.

The products of the present invention can also be salified with potassium lithium, calcium, barium or magnesium, or can be salified with organic bases such as medium- or long-chain amines.

For the salification with cations other than sodium, the usual procedure consists in the liberation of heparinic acid or of the acids corresponding to dermatan sulfite or heparan sulfate on a cation exchange column, and in the subsequent salification with the desired cation.

The oligosaccharides of the present invention have mainly the reducing terminal groups of the $C_1$ carbon of the V and VI type.

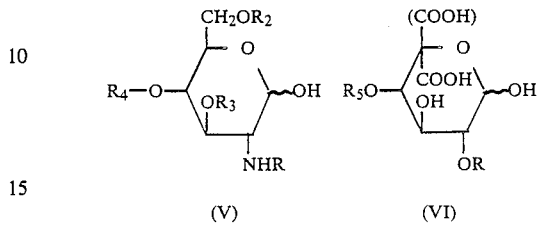

For Heparin and Heparan Sulfate
$\begin{cases} R = SO_3H, Ac \\ R_1 = R_2 = R_3 = H, SO_3H \\ R_4 = \text{Uronic Acid} \\ R_5 = \text{Aminosugar} \end{cases}$ For Dermatan Sulfate
$\begin{cases} R = Ac \\ R_1 = R_2 = H \\ R_3 = \text{Uronic Acid} \\ R_4 = SO_3H \\ R_5 = \text{4.0 Sulfated N-acetylated Galactosamine} \end{cases}$ just like the natural oligomers of heparin and of the other polysaccharides obtained by chromatographic fractionation or by selective precipitation.

Said terminal groups, however, can be easily oxidized to aldonates, for example with NaIO, or reduced to alcohols, for example with $NaBH_4$.

The process object of the present invention, does not change the content of the $-SO_3H$ groups, important for the biological activity, as it turns out from the $-SO_3H$ eq/$-COOH$ eq ratio deduced in the depolymerization products as compared with the starting products.

Said process, moreover, is characterized by the possibility of being kept under control and stopped at the desired rate of depolymerization, with consequent substantial advantages that will appear evident to the expert of the art.

The process is controlled by assessing the mean molecular weight or an oligomer s biological activity, directly related with its mean molecular weight, such as for example the APTT (Activated Partial Thromboplastin Time) or activated anti-Factor X activity.

The process can be stopped at will by lowering the reaction pH or the temperature or by discontinuing the production of radicals or by inhibiting with a known inhibitor such as SOD, catalase, p-oxybenzoates.

The products of the present invention show a mean molecular weight ranging between 2,000 and 7,000 daltons.

The present invention also concerns all the aspects, applicable on an industrial scale, associated with the use of the products, resulting from the process of the invention. For human therapeutic applications such as antithrombotic, fibrinolytic and antiinflammatory agents, with poor or no anticoagulant activity; for the purpose, the compounds, that are the object of the present invention, are formulated, by conventional techniques and excipients, as pharmaceutical compositions suited for parenteral, topical and oral administration.

Examples of formulations, suited for parenteral administration, include sterile solutions contained in ampuls.

Examples of formulations, suited for oral administration, include capsules, tablets and syrups, wherein the active ingredient may also be vehiculated in form of liposomes or micelles.

Examples of topical formulations are provided by ointments comprising the usual excipients known in the art.

The below reported examples illustrate the invention with no limitation to its scope.

EXAMPLE 1

305 Grams of HFA 116-7 raw heparin, together with 300 g of sodium chloride and 300 g of sodium acetate dihydrate, are poured into a reaction vessel, with 2 liters of water.

As soon as dissolution has occurred, a salt is added, correspondent to 4.35 g of divalent copper dissolved in 300 ml of water. A solution of 1000 ml of 15% hydrogen peroxide and a normal solution of NaOH are dropped separately, under constant stirring, in order to keep pH at a 7.5 value in the course of the reaction. Dropping and stirring are continued for 2 hours; the temperature of the reaction mass is kept at 45°–60° C. The reaction mass is then cooled down to room temperature, and added with 17 g of disodium ethylenediaminetetraacetate dihydrate (EOTA); the pH is adjusted at a 5.9 value with acetic acid.

Depolymerized heparin is precipitated with 7.9 liters of methanol; the precipitate, collected on a filter, is dissolved again in 4 liters of water, and added with 75 g of sodium acetate monohydrate and 4 g of EDTA. The resulting solution, adjusted to pH 5.8 with acetic acid, is treated with 8 liters of methanol; the resulting precipitate is collected by filtration, washed with methanol and acetone, and dried.

255 Grams (83.6% yield) are obtained of a low molecular weight white heparin (OP 85/0201), having the following characteristics: mean molecular weight: 4200 (Hilborn J. C. and Anastassiadis, Anal. Biochem. 39, 88, 1971); U-ApTT 33,19 (Basu D. et al., N. Engl. J. Med. 287, 324, 1972): U-aXa 81.7 (Teien A. N. et al., Thromb. Res., 8, 413, 1976). The starting raw heparin had respectively the following characteristics: 13,700; 170.7; 166.8.

EXAMPLE 2

200 Grams of 116.7 HFA heparin are introduced into a thermostatized reaction vessel, together with 200 g of sodium acetate trihydrate and 200 g of sodium chloride. 2100 Ml of a 0.02M solution of a cupric copper salt are added. When dissolution has occurred, 500 ml of 19% hydrogen peroxide and N NaOH are separately dropped, in a 15 minutes interval of time, in order to keep the pH of the reaction mass at a 7.2. In the inner reaction vessel, the temperature ranges between 35° and 50° C.

30 Grams of sodium EOTA are added 60 minutes after starting the reaction; the solution is adjusted with acetic acid at pH 5.9, and the product is precipitated with 2 volumes of MetOH.

The precipitate is washed with acetone, and immediately dissolved again (with no drying) in 2 liters of water. 5 Grams of EDTA and 50 g of sodium acetate are added. The pH is adjusted to 6, and 2.5 volumes of MeOH are added under stirring.

After filtration, anhydrification with acetone and drying, 183 g are obtained of raw product, coded OP84/2610, in a 91.5% yield, having the characteristics shown in Table 1.

TABLE 1

| Product | In vitro act. U-APTT | U-aXa | In vivo act. Ant. I.V. act. | M.W. | S % | Uronic acid % | $\frac{\text{eq}^-SO_3H}{\text{eq}^-COOH}$ |
|---|---|---|---|---|---|---|---|
| Hep 116.7 | 170.7 | 166.8 | 135 | 13700 | 10.6 | 26.7 | 2.39 |
| Es. 1 OP84/2610 | 32.1 | 72.3 | 127 | 3480 | 11.0 | 26.1 | 2.56 |

The copper content results to be 3.93 ppm.

The antithrombotic activity (Ant. Act.) was assessed in vivo according to the method of Reyers S., Mussoni L., Donati M. B., De Gaetano G., Thromb. Res. 18, 699, 1980, following intravenous administration. Sulfur and uronic acids were measured potentiometrically, after removing a possible inorganic acidity by chromatography on an anionic column (OH$^-$ form), and liberation of heparinic acid through transfer on a cationic column (H$^+$). The ratio between the two titration flexures corresponds to the $^-SO_3H$ eq/$^-COOH$ eq.

Bioavailability following oral administration

When the product is administered through the intraileal route, by a suited vehicle consisting of a lipid phase and a surfacant agent suited to ensure a stable micellar system (Stanzani L., Mascellani G., Corbelli G. P., Bianchini P., J. Brit. Pharmacol., 33, 783, 1981), in the venous thrombosis model according to Reyers et al., the below reported ED 50 are obtained for halving the thrombi weights.

HFA 116.7=7.5 mg/kg
OP 84/2610=3.25 mg/kg.

EXAMPLE 3

Into a reaction vessel fitted with a thermostatized bath, stirrer, calibrated drop funnels and thermometer, 1 kg of HFA 15 raw heparin, 0.495 kg of sodium chloride, and 1 kg of sodium acetate are introduced and dissolved with 10 liters of water. 46 Grams of copper acetate monohydrate dissolved in 1 liter of water are then added, the temperature is adjusted to 35° C. and within a 2.5-hours time, a solution of N NaOH thereto in order to adjust the pH at 7.5, and a 9% hydrogen peroxide solution are separately added. The inner temperature is concurrently checked so as to allow an excursion from 35° C. to 60° C.

In the course of the reaction, samples are taken out at regular intervals of time in order to check the parameters pertaining to the in vitro activity (U-APTT and U-aXa) and to the mean molecular weight.

At the end of the reaction, 90 g of EDTA are added, the pH is adjusted at 5.9 with 30% acetic acid, and 44 liters of methanol are added to the reaction mass.

The formed precipitate is collected by filtration, washed with methanol, and dissolved again in 10 liters of water.

The resulting solution is added with 350 g of sodium acetate, 20 g of EDTA and, after adjusting the pH at a 5.8 value, added with 20 liters of methanol. The formed precipitate is collected, washed with methanol and acetone, and dried. 845.5 Grams (84.5% yield) are obtained of a low molecular weight white heparin, having the following characteristics:
molecular weight: 4,600 daltons
U-APTT 34.4
U-aXa 72.5.

The pattern of the mean molecular weights of the oligomers, at the various stages of the present process, as well as the related analytical characteristics and biological activities, are reported in the following Table 2.

TABLE 2

| TIMES | Mean M.W.* | U-APTT* | U-aXa | S % | Uronic acids % | eq$^-$SO$_3$H / eq$^-$COOH |
|---|---|---|---|---|---|---|
| 0 | 13400 | 126.7 | 107.1 | 8.72 | 25.82 | 2.05 |
| 15' | 11200 | 98.4 | | | | |
| 30' | 9400 | 86.9 | | | | |
| 60' | 8100 | .62 | 89.6 | 9.58 | 27.96 | 2.07 |
| 90' | 6900 | 50.2 | | | | |
| 120' | 5200 | 36 | 73 | | | |
| Raw precipitate | 4600 | 34 | 73 | 9.65 | 28.16 | 2.08 |

*The equation of the correlation line between the mean M.W. (X) and U-APTT (y) is the following: y = 0.0108055 x −20.1658 (r = 0.9925)

The resulting raw product is dissolved in 6 liters of water, and percolated on an anionic exchange resin column, highly basic in an OH$^-$ form (amberlite type) (100$\phi$×650 mm) at the rate of 2 volumes/hour approximately. The eluate is added with acetic acid to pH 5, and percolated on 2 liters of a mildly acid chelating resin.

The eluate, following precipitation with methanol, gives 803.2 g of a highly purified low molecular weight heparin (LMW OP 144). The atomic absorption test proved the absence of copper.

The signals of the reducing terminal groups appear in the anomeric area of the $^{13}$C-NMR spectrum, recorded at 20 MHz in D$_2$O, i.e. C-1 of N-sulfated glucosamine ($\delta$92.7 ppm) and 2.0 sulfated iduronic acid (94.4 ppm), in comparison with methanol as internal standard, whose chemical shift is 51.75 ppm.

EXAMPLE 4

25 Grams of heparin previously depolymerized (OP84/0410) by a process analogous to the one specified in the Example 3, having the following characteristics: (U-APTT/mg=7; U-aXa/mg=52. in vivo antithrombotic activity 116, molecular weight 3300) are subjected to a process of further depolymerization, as hereinbelow specified.

25 Grams of said LMw-heparin are poured into 200 ml of water, with 0.75 g of copper acetate. 180 Ml of 16% hydrogen peroxide are then added within 2 hours, under stirring, at a temperature of 65°-70° C. The pH is kept at 7.4, by means of NaOH. The resulting solution is cooled, adjusted to pH 6, transferred on a chelex 100 ® column (2.8$\phi$×13 cm), then on an amberlite ® column (IRA. 400 OH$^-$ form, 4.2$\phi$×8 cm) and subsequently on a polystyrene column, strongly acid in a H$^+$ form.

The eluate is adjusted with NaOH to pH 7, and freeze-dried. 19.55 Grams (78.2 yield) are obtained of a low molecular weight OP 119 heparin: its characteristics, compared with the ones of the starting product, are reported in Table 3.

TABLE 3

| Product | M.W. | S % | Uronic acid % | eq$^-$SO$_3$H / eq$^-$COOH |
|---|---|---|---|---|
| P85/0410 | 3200 | 10.78 | 31.23 | 2.09 |
| VLMW OP 119 | 1700 | 7.3* | 20.8* | 2.12 |

NOTE:
*An aliquot of the very low molecular weights was kept back from the anionic column: this evidence explains the decrease in the percent values of sulfur and uronic acids. Actually, the $^-$SO$_3$ eq/$^-$COOH eq values proved to be unchanged.

The $^{13}$C-NMR spectrum shows, at 92.7 ppm, a very evident signal ascribable to the anomeric carbon of N-sulifated glucosamine; signals, possibly ascribable to the C$_1$ carbons of glucuronic acid and iduronic-2-O-sulfate respectively, appear at 90.9 and 94.4 ppm.

EXAMPLE 5

10 grams of dermatan sulfate (060284 Ac/sol) having mean molecular weight of about 12,000 for 50% and >25,000 for 50% about and having 21 U antithrombotic activity and 1.7 and 17 U-APTT and U-aXa, respectively, are poured into 100 ml of water, together with 10 g of sodium chloride and 10 g of sodium acetate. 0.45 Grams of copper acetate monohydrate are added. When dissolution has occurred, 20 ml of 24% hydrogen peroxide are added within 40 minutes, keeping temperature between 25° and 47° C., and pH at 7.6 with NaOH.

Stirring is continued for 20 further minutes; 0.5 g of EDTA are added, and the pH is adjusted to 6 with acetic acid; the depolymerized product is precipitated with 2 volumes of methanol. The solid residue is collected by filtration, and dissolved again in 100 ml of water. After addition of sodium acetate and 0.45 g of EDTA, and adjustment of the pH to 6, the compound is precipitated again with methanol. Following filtration, the collected solid residue provides, after drying, 7.1 g (71% yield) of a low molecular weight dermatan sulfate. The product, subjected to a chemical and biological analysis, provided the following data.

Mean molecular weight: 3000-2800
S %: 7.4
Uronic acids %: 28.9
eqSO$_3$/eq$^-$COOH: 1.4
"In vitro" activity U-APTT: ≃1
U-aXa: 29
"In vivo" antithrombotic activity: 35.

Dermatan sulfate 060284 was fractionated on a Cellex D OEAE cellulose column, activated with 0.5N HCl, under the following conditions. 8 Grams of dermatan sulfate were chromatographed on a column (2.5$\phi$×55 cm) balanced with 0.1M NaCl. Elutions were carried out with 2 liters of 0.1M, 0.3M and 1.5M solutions of NaCl. The eluates were concentrated, and dermatan sulfate was precipitated with two volumes of methanol.

The tested fractions, together with their fractionation yields and characteristics, are reported in Table 4.

TABLE 4

| Fract. | Yield % | M.W. | S % | Ur. Ac. % | $\dfrac{\text{eq}^-SO_3H}{\text{eq}^-COOH}$ | In vitro act. U-APTT | In vitro act. U-aXa | In vivo act. Ant. ac. |
|---|---|---|---|---|---|---|---|---|
| Unfract. | | 12000<br>>25000 | | | | 1.7 | 17 | 21 |
| 0.1 M | 26.1 | 12000<br>20000 | | | | | | |
| 0.3 M | 21.2 | 12000<br>4000 | 6.9 | 28.2 | 1.49 | 2.6 | 38 | 48.7 |
| 1.5 M | 36.7 | 12000 | 6.8 | 28.8 | 1.42 | 3.0 | | 28.7 | product are obtained, having the characteristics shown in the herein reported Table 5.

TABLE 5

| Product | M.W. | U-APTT | U-aXa | S % | Ur. Ac. % | $\dfrac{-SO_3H}{-COOH}$ |
|---|---|---|---|---|---|---|
| HS 436-7/08 | 20800 | 5.32 | 19.45 | 5.95 | 23.52 | 1.53 |
| LMW HS | 5300 | | 10.49 | 5.45 | 22.05 | 1.48 |

Depolymerization allows to obtain in a good yield oligomers having a satisfactory activity, otherwise only attainable in a very low yield through highly time-consuming fractionations.

The depolymerization products are moreover endowed with a fibrinolytic activity.

EXAMPLE 6

5 Grams of heparin, with a mean molecular weight of 13,700 daltons, are dissolved in 100 ml of water, with 10 g of sodium acetate. 15 Ml of a 0.32M solution of ferrous sulfate are added, and 50 ml of 5.4% hydrogen peroxide dropped thereafter within 40 minutes. The temperature of the reaction mass is kept at 60° C. The pH is adjusted to 7.5 with NaOH. The reaction mass is cooled, and filtered on decalite. The filtrate is added with 0.6 g of EOTA, and the product precipitated with 300 ml of methanol. The precipitate is collected by filtration, and dissolved again in 300 ml of water. 0.6 Grams of EOTA and 18 g of sodium acetate are added; the resulting mass is reprecipitated with 600 ml of methanol. The depolymerization product, collected by filtration, gives after drying 4.6 g (92% yield) of heparin with a molecular weight of 7,950.

EXAMPLE 7

2 Grams of OP 436-7/08 heparan sulfate, with a molecular weight of 20,800, are dissolved in 30 ml of water, together with 92 mg of copper acetate monohydrate. 5 Ml of 7.2% hydrogen peroxide are dissolved within 60 minutes, keeping the pH to 7 with sodium hydroxide, and the temperature at 50° C.

At the end of the reaction, 2 g sodium acetate, 100 mg of EDTA and 100 ml of ethanol are added. The formed precipitate is collected by filtration, washed with methanol, and redissolved in 15 ml of water. The solution is acidified with acetic acid up to a 4.5 pH value, and eluted on a IRC 718 amberlite resin column (1.2$\phi$ × 12 cm); the eluate is added with 0.45 g of sodium acetate at pH 5.5, and finally with 30 ml of methanol.

The depolymerized heparan sulfate precipitates, which is collected and dried. 1.18 Grams (59% yield) of

EXAMPLE 8

5 Grams of raw heparin, with a molecular weight of 14,500 daltons are poured into 100 ml of a 0.01M solution of a divalent copper salt, containing 5% of sodium chloride and 5% of sodium acetate. 50 Ml of a 1.6M solution of sodium persulfate are added under stirring, heating at The pH is kept at the approximate value of 7 with sodium hydroxide. The solution is cooled. The crude reaction product is precipitated with 350 ml of methanol; the precipitate is dissolved again in 50 ml of water, eluted on an anionic exchange resin (4.2$\phi$ × 15 cm) in the $-OH$ form, and subsequently on a cationic exchange resin in the $H^+$ form (4.2$\phi$ × 10 cm). The eluate, neutralized at pH 7 and added with 3 g of sodium acetate, is treated with 200 ml of methanol.

The precipitate, collected by filtration, gives after drying 3.47 g (69.5% yield) of highly purified heparin with a molecular weight of 3,900.

EXAMPLE 9

Salification with calcium

200 Grams of OP 146 LMw heparin, with a mean molecular weight of 4,700, 28.4 U-APTT/mg, 88.67 U-aXa/mg with 9.55% of sulfur, 27.8% of uronic acids and a $R_3$ ratio = $SO_3H$ eq/COOH eq = 2.08 (assayed potentiometrically) are poured into 2000 ml of water, and percolated on a column (4.2$\phi$ × 100 cm) containing a strongly acid polystyrene resin in the $H^+$ form.

The markedly acid eluate had been constantly neutralized with a solution of calcium hydroxide. At the end of the percolation process, 60 g of calcium chloride were added, and the LMW calcium heparin precipitated with 2 volumes of methanol.

After drying, 191 g of OP 149 Ca (95.5% yield) calcium heparin were obtained, showing a molecular weight of 4,600 daltons and the following characteristics:

S = 10.63%, Uronic acid = 28.78%, R = 2.24 (potentiometric assays).

Ca = 9.58% (by atomic absorption)

Na=0% (by atomic absorption)
U-APTT=25.2/mg; U-aXa=84.2/mg (assays by the chromogenic method).

The preparation resulted to be pyrogen-free.

EXAMPLE 10

Heparan, depolymerized according to the present process (OPI18 K having 94.81 U-aXa (cromogenic) per mg and 29.92 U-APTT/mg), was given to rats, by the intraileal route, at the dose of 35 mg/kg, in comparison with heparan (non-depolymerized) given at the same dose. Samples were collected at intervals, and the anti-activated Factor X activity (aXa) was assayed in the plasma of rats. The plasma levels are reported in the following Table 6.

TABLE 6

| Product | N# | min. | mcg/ml | AUC |
|---|---|---|---|---|
| LMW/OP118K | 1 | 0 | 0 | |
| | 2 | 15 | 13.9 | |
| | 3 | 30 | 19.1 | |
| | 4 | 60 | 32.3 | 3585.7 |
| | 5 | 90 | 26.5 | |
| | 6 | 120 | 11.7 | |
| | 7 | 240 | 5.1 | |
| Heparin | 1 | 0 | 0 | |
| | 2 | 15 | 1.9 | |
| | 3 | 30 | 2.4 | |
| | 4 | 60 | 4.6 | 426 |
| | 5 | 120 | 0.95 | |
| | 6 | 240 | 0.85 | |

The obtained LMW has a bioavailability 8 times as high as that of the molecular weight heparan, according to the comparisons of the areas under the curve (AUC).

EXAMPLE 11

Dermatan sulfate (DS), depolymerized according to the conditions of the Example 5, provided the chemical and activity characteristics shown in the following Table 7, as compared with the characteristics of the undepolymerized product.

TABLE 7

| Product | U-APTT | U-aXa | M.W. | S % | Uronic acids | $\frac{SO_3H}{COOH}$ |
|---|---|---|---|---|---|---|
| DS | 3.7 | 24.1 | 14000 | 6.8 | 27.4 | 1.51 |
| LMW-DS | 5.2 | 25.3 | 3000 | 7.7 | 27.8 | 1.67 |

Following an intraileal administration, given to rats in the experimental thrombosis model, LMW-DS provided an $ED_{50}$ (for halving the thrombi weight) of 6.9 mg/kg versus 8.9 mg/kg of the undepolymerized DS. LMW-DS also proved to be fibrinolytic.

EXAMPLE 12

Grams of dermatan sulfate OP 239 (formed by following mixture of molecular weights: 19% >20,000, 30%≃14,000, 50%≃12,000, determined by HPLC) and having $[\alpha]_D = -60$ are placed in 100 ml of water, together with 250 mg of acetate copper.

30 Ml of 15% hydrogen peroxide are added during the period of an hour at a temperature between 37° and 40° C. pH is kept at 7.5 with total 14 ml of NaOH N.

At the end of the reaction the solution is cooled at 20° C. and pH is lowered at 5.8 with acetic acid.

Two volumes of methyl alcohol are added and the so obtained precipitated is isolated by filtration. Then it is solubilized in 60 ml of water and eluted on Chelex 100 ® Resin ($\phi$2, h 18 cm). The obtained solution, together with the washing water of the column, is added with 2 volumes of ethanol. The precipitated, isolated by filtration and dried up, gives 6.11 g (61% yield) of dermatan sulfate with the following features:

$[\alpha] = -59.3$; S=6.7%; Iduronic acids=30.7%;

$$\frac{eq\ SO_3H}{eq\ COOH} = 1.32$$

Medium molecular weight=4,800 Daltons (by HPLC on Protein Pak 125 column (Waters))

$^{13}$C-NMR chemical shifts are given with respect to external tetramethylsilane, using methanol as an internal reference. The chemical shift of methanol in $D_2O$ relative to that of tetramethylsilane was 51.75 ppm.

Chemical shifts of L-idosyluronic acid (U) and of acetamidodeoxy-O-galactose (A), with the indication of the carbon atoms to which they belong, are given: $\delta$(ppm): 104.8 ($U_1$), 103.6 ($A_1$), 82 ($A_3$), 77.73 ($U_4$), 76.94 ($A_4$), 76.08 ($A_5$), 72.7 ($U_3$), 70.9 ($U_{2-5}$), 60.72 ($A_6$), 52.9 ($A_2$), 25.7 ($CH_3$).

In the range 90-95 ppm the signals of the reducing end-groups ($A_1$ and $U_1$) are evident.

The in vitro compound gives: U-aXa=2.5 U.I./mg and U-APTT=1.3 U.I./mg.

In the kaolin experimental thrombosis according to Hladovec (Physiologia Bohemoslovaca, 24, 551, 1975): it has given $ED_{50} = 1.2$ mg/kg e.v.

EXAMPLE 13

5 Grams of dermatan sulfate 7–8 HF having molecular weight >34,000 (by HPLC) are placed in 100 ml of water, together with 5 g of sodium acetate.

230 Mg of monohydrate cupric acetate are added and then 20 ml of 12% hydrogen peroxide are dropped for an hour.

The temperature is kept between 30° and 38° C. and pH is kept at 7.5 with total 5 ml of NaOH 0.1N.

At the end of the reaction 500 mg of dihydrate bisodic EDTA are added, pH is adjusted at 5.9 with acetic acid and the depolimerization product is precipitated with 2 volumes of methyl alcohol.

The product is, then, worked out as in the previous Examples.

2.95 Grams of OP 116 (59% yield) are obtained. Product features:

S=6.16%; Uronic acids=30.84%;

$$\frac{eq\ SO_3H}{eq\ COOH} = 1.21$$

M.W.=≃6,000 Daltons, determined by HPLC on Protein Pak 125 column (Waters), flux 1 ml/minute, phase: mobile 0.125M $Na_2SO_4$ buffered at pH 6 with $Na_2HPO_4/NaH_2PO_4$ 2 mM. Refraction index Detector.

$^{13}$C-NMR (TMS as external standard and methanol as internal standard with chemical shift 51.75 ppm): $\delta$ppm 104.8 (C-1 iduronic acid), 103.37 (C-1 amino-sugar-4.0-sulfate); 60.72 (C-6 amino-sugar-O-sulfate); 52.95 (C-2 amino-sugar N.Ac.).

$[\alpha] = -60$ (in water)

"In vivo" antithrombotic activity: 24.7 U.

"In vitro" U-APTT: 2 U.I./mg.

What is claimed is:

1. The oligosaccharide fraction from dermatan sulfate which has molecular weight 4800 daltons, U-aXa 2.5 U.I./mg. and UAPTT 1.3 U.I./mg, $$\frac{-SO_3H}{COOH} = 1.32.$$

2. The oligosaccharide fraction from dermatan sulfate which has: a 6,000 D molecular weight, $SO_3^-/COO^-$ ratio 0.9÷1.2, AXa 1÷10 U/mg, and antithrombotic, thrombolytic, fibrinolytic, antiinfammatory activities in vivo.

3. A pharmaceutical composition with an antithrombotic, antiinfammatory, fibrinolytic activity, comprising as the active ingredient, the oligosaccharide fraction according to claim 2, and pharmaceutically acceptable excipients, in the form of a sterile injectable solution or a suspension, capsule, tablet or syrup.

* * * * *